United States Patent
Buiser et al.

(10) Patent No.: US 8,726,931 B2
(45) Date of Patent: May 20, 2014

(54) POWER INJECTABLE VALVE DESIGNS

(75) Inventors: Marcia Buiser, Marlborough, MA (US);
Damon Casiello, Lowell, MA (US);
Charles R. Aubin, Plainville, MA (US);
Paul E. Karnafel, Foxborough, MA (US)

(73) Assignee: Navilyst Medical, Inc., Marlborough, MA (US)

(*) Notice: Subject to any disclaimer, the term of this patent is extended or adjusted under 35 U.S.C. 154(b) by 388 days.

(21) Appl. No.: 13/082,569

(22) Filed: Apr. 8, 2011

(65) Prior Publication Data
US 2012/0256114 A1 Oct. 11, 2012

(51) Int. Cl.
*F16K 15/14* (2006.01)
*A61M 39/24* (2006.01)

(52) U.S. Cl.
CPC .............. *F16K 15/144* (2013.01); *F16K 15/147* (2013.01); *A61M 2039/2433* (2013.01); *A61M 2039/2426* (2013.01)
USPC ....................... 137/512.15; 137/845; 137/859

(58) Field of Classification Search
CPC .............. A61M 2039/2426; A61M 2039/2433; A61M 39/24; F16K 15/144; F16K 15/147
USPC .............................. 137/512.15, 844, 845, 859
See application file for complete search history.

(56) References Cited

U.S. PATENT DOCUMENTS

| | | | | |
|---|---|---|---|---|
| 1,989,145 | A | * | 1/1935 | Newby ........................... 222/498 |
| 2,122,299 | A | * | 6/1938 | Sloan ............................. 222/490 |
| 3,811,466 | A | * | 5/1974 | Ohringer ....................... 137/493 |
| 3,827,456 | A | * | 8/1974 | Sheppard ...................... 137/859 |
| 3,964,509 | A | * | 6/1976 | Daubenberger et al. ...... 137/844 |
| 4,176,678 | A | * | 12/1979 | Marchaix et al. ............. 137/493 |
| 5,000,745 | A | * | 3/1991 | Guest et al. ................... 604/256 |
| 5,843,044 | A | | 12/1998 | Moorehead |
| 5,984,902 | A | | 11/1999 | Moorehead |
| 6,293,437 | B1 | * | 9/2001 | Socier et al. .................. 222/212 |
| 6,416,499 | B2 | * | 7/2002 | Paul, Jr. ......................... 604/256 |
| 7,172,580 | B2 | * | 2/2007 | Hruska et al. ................. 604/248 |
| 2005/0027261 | A1 | | 2/2005 | Weaver et al. |
| 2005/0171488 | A1 | | 8/2005 | Weaver et al. |
| 2005/0171489 | A1 | | 8/2005 | Weaver et al. |
| 2005/0171490 | A1 | | 8/2005 | Weaver et al. |
| 2009/0177187 | A1 | | 7/2009 | Weaver Quigley et al. |

* cited by examiner

*Primary Examiner* — Craig Schneider
(74) *Attorney, Agent, or Firm* — Ryan D. Artis

(57) ABSTRACT

Pressure activated valves for catheters with improved tolerance of high pressure and high flow conditions are described. Embodiments of the valve comprise a flexible membrane with one or more linear slits therethrough, and means for applying tension to the flexible membrane in-line with the linear slits. The application of tension may optionally be facilitated by structural features of both the flexible membrane and the valve housing.

15 Claims, 6 Drawing Sheets

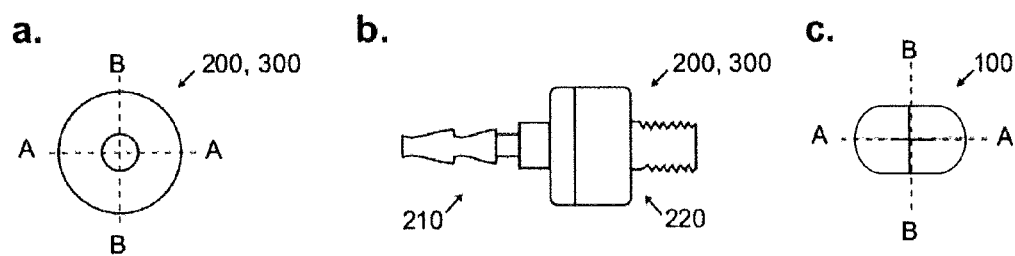
Figure 3 a-c

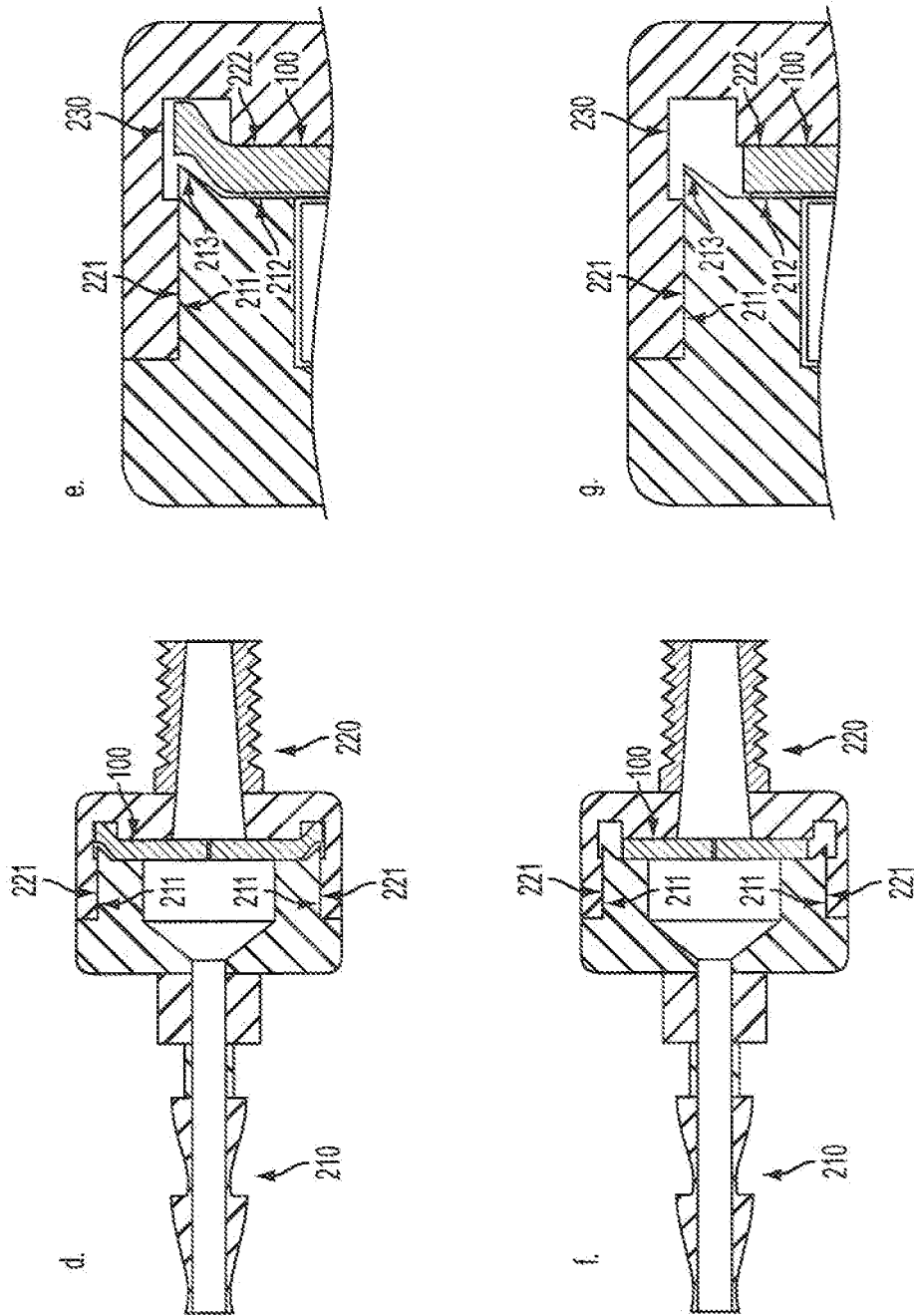
Figure. 3 d-g

POWER INJECTABLE VALVE DESIGNS

The present application incorporates by reference the entire disclosure of U.S. Pat. Nos. 5,843,044 and 5,984,902, both entitled "Outdwelling slit valve and variable control for controlling opening and closing the slit" and both naming H. Robert Moorehead as inventor. The present application also incorporates by reference the entire disclosure of: (i) U.S. Publication No. 2005/0171489, entitled "Pressure activated safety valve with anti-adherent coating" and naming Karla Weaver and Paul DiCarlo as inventors; (ii) U.S. Publication No. 2005/0171488, entitled "Pressure activated safety valve with high-flow slit" and naming Karla Weaver and Paul DiCarlo as inventors; (iii) U.S. Publication No. 2005/0171490, entitled "Stacked membrane for pressure actuated valve" and naming Karla Weaver and Paul DiCarlo as inventors; (iv) U.S. Publication No. 2009/0177187, entitled "Pressure activated valve with angled slit" and naming Karla Weaver Quigley, Steven Grantz, Richard Pok, Anthony Hien and Kimberly Un as inventors; and (v) U.S. Publication No. 2005/0027261, entitled "Pressure actuated valve with improved slit configuration" and naming Karla Weaver and Jim Culhane as inventors.

FIELD OF THE INVENTION

The present invention relates to valves for catheters such as the PASV® valve technology commercialized by Navilyst Medical, Inc.

BACKGROUND OF THE INVENTION

Many medical procedures, such as chemotherapy, intravenous antibiotic therapy, and parenteral nutrition administration, require repeated and prolonged access to a patient's vascular system. Because it may be impractical or even dangerous to insert and remove a needle or catheter each time vascular access is needed in these applications, treatments requiring repeated vascular access over long periods of time utilize implantable vascular access catheter assemblies.

A vascular access catheter assembly may be implanted semi-permanently, with a distal end of the assembly remaining within the patient in contact with the vascular system while a proximal end remains external to the vasculature, for example in the form of a subcutaneously implanted port or an outdwelling proximal catheter access point. The proximal end is sealed when not in use to prevent blood loss and infections.

A common method of sealing an implanted catheter after use is to shut the catheter with a simple clamp. This method is often unsatisfactory because the repeated application of the clamp may weaken the walls of the catheter due to the stress placed on the walls at a single point. In addition, the pinched area of the catheter may not be completely sealed. Alternatively, pressure activated valves have been used at the proximal ends of catheters. Pressure activated valves seal rapidly and reliably without any operator input, do not affect catheter patency even after many opening and sealing cycles, and can tolerate the relatively low pressures and flow rates required for many applications for long periods of time. However, certain applications, such as infusion of contrast media for contrast-enhanced CT scanning require very high pressures and flow rates which may damage currently available pressure activated valves. It would be desirable to provide a pressure activated valve for a catheter with improved tolerance of high pressures and high flow rates.

SUMMARY OF THE INVENTION

In one aspect, the present invention addresses the need described above by providing a pressure activated valve with improved suitability for high pressure injection. In some embodiments, the present invention comprises a valve apparatus for medical applications including a valve housing that defines a lumen and has first and second valve housing portions, which valve housing portions have first and second mating surfaces that are in contact with one-another, and a flexible membrane with one or more linear slits. The mating surfaces define a space that is in-line with an axis defined by a slit through the membrane and is sized to accommodate a portion of the membrane.

In other embodiments, the present invention comprises a valve apparatus comprising a flexible membrane with one or more linear slits and one or more tabs positioned in-line with at least one of the linear slits.

In still other embodiments, the present invention comprises a valve apparatus comprising a flexible membrane with a central portion with a first thickness, which comprises one or more linear slits, and an edge portion with a second thickness, which edge portion is in-line with at least one of the linear slits of the central portion, where the second thickness is greater than the first thickness.

BRIEF DESCRIPTION OF THE DRAWINGS

In the drawings, like reference characters generally refer to the same parts throughout the different views. Drawings are not necessarily to scale, as emphasis is placed on illustration of the principles of the invention.

FIG. 2a is a top view, FIG. 2b is a perspective view, and FIGS. 2c-2f are side views.

FIGS. 3a-g are top, side and cross-sectional views of a valve according to an embodiment of the present invention. FIGS. 3a and 3c are top views of a flexible membrane, FIG. 3b is a side view of a valve housing, and FIGS. 3d-3e are cross sectional views of a valve housing.

DETAILED DESCRIPTION OF THE PREFERRED EMBODIMENTS

Throughout this specification, for purposes of illustrating the principles of the invention, reference is made to valves with substantially planar, flexible membranes having a single, linear slit as a flow control mechanism. However, it will be understood by those skilled in the art that the invention is compatible with a variety of slit arrangements, including membranes having a plurality of linear slits, and membranes having slits which extend through the thickness of the flexible membrane at an angle relative to the planes defined by the surfaces of the membrane, as described in United States Publication No. 2009/0177187.

The present invention provides pressure activated valves having improved tolerance of high-pressure injection conditions. The invention utilizes flexible membranes incorporating one or more linear slits as flow-control elements, and structural features which selectively apply tension to the membrane along axes defined by the linear slits. The tensioning force applied by these features helps the edges of the slits resist the pressures applied during high-pressure injections without deforming and helps bias the edges to return to their ordinary, closed positions without puckering or folding once the high pressure injection has stopped.

Figure 1:
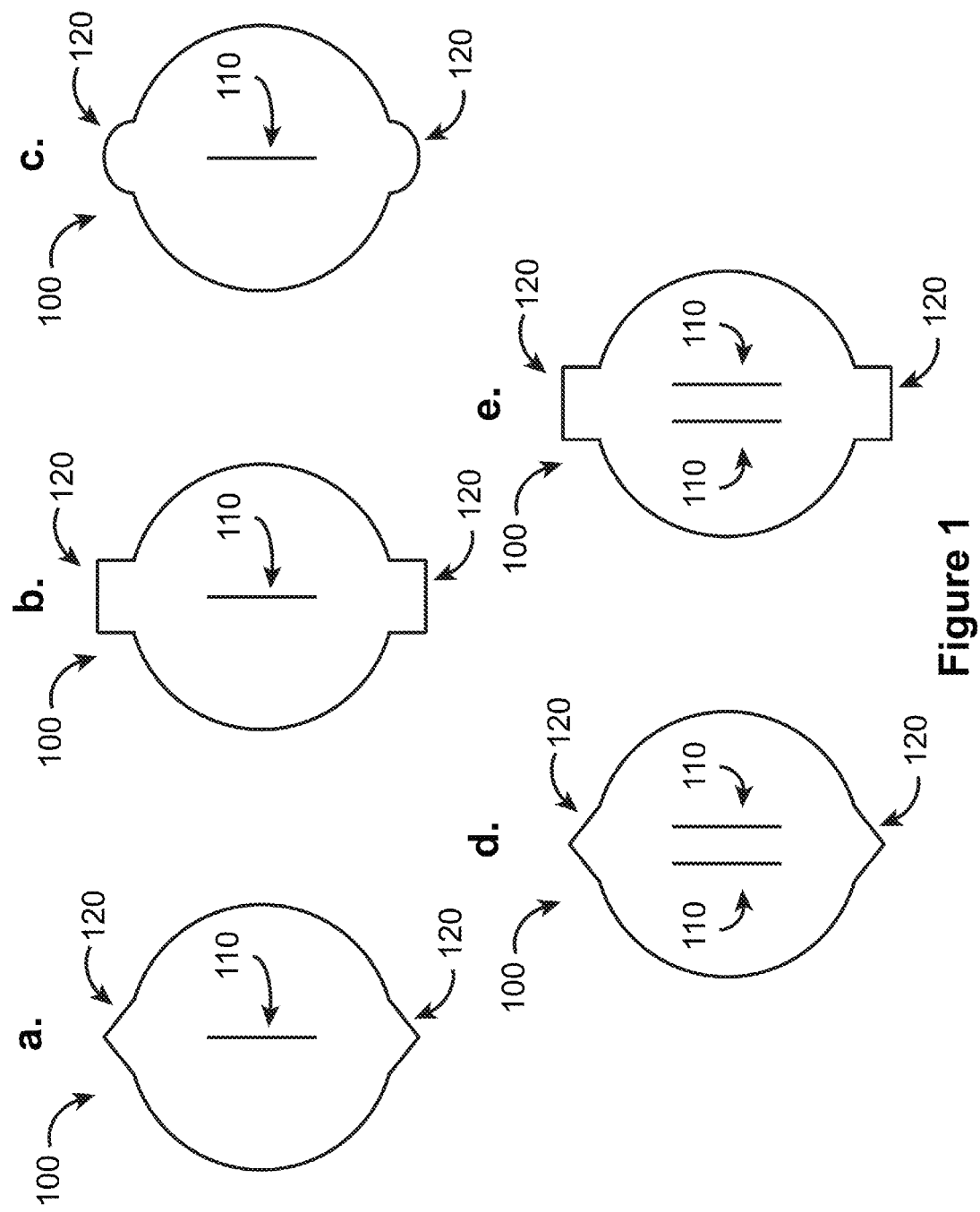
FIGS. 1a-e show top views of flexible membranes with tabs according to certain embodiments of the present invention.

In certain embodiments, tension is selectively increased about an axis defined by a slit in a flexible membrane through the incorporation of one or more tabs into the membrane, which tab or tabs are positioned along the longitudinal axis defined by the slit as shown in FIGS. 1a-c. Although the membrane may incorporate a plurality of linear slits and may be any suitable shape, in the embodiments shown in FIG. 1 a-c, the flexible membrane 100 has a single linear slit 110 and is substantially round except for two tabs 120 positioned along an axis defined by the linear slit 110. In alternate embodiments, the flexible membrane incorporates multiple parallel linear slits and multiple tabs positioned in-line with the slits.

The tab or tabs 120 may be angular as in FIGS. 1a and 1d, rectangular as in FIGS. 1b and 1e, curved as in FIG. 1c, or any other shape suitable for applying tension along the axis defined by the linear slit 110. When the tabs 120 are compressed, stretched, or folded, preferably by membrane-securement features of the valve housing, tension is applied along the axis of the slit 110. Any suitable membrane-securement features known in the art can be used to compress, stretch or fold the tabs 120, including but not limited to flanges, ridges, adhesives, epoxies, fasteners, compression rings, stacked membranes, mating surfaces, and combinations of the above. These membrane-securement features can compress, stretch or fold the edges of the flexible membrane 100 uniformly, but in preferred embodiments the membrane-securement features compress, stretch or fold the tabs 120 to a greater degree than the other edges of the flexible membrane 100.

Figure 4:
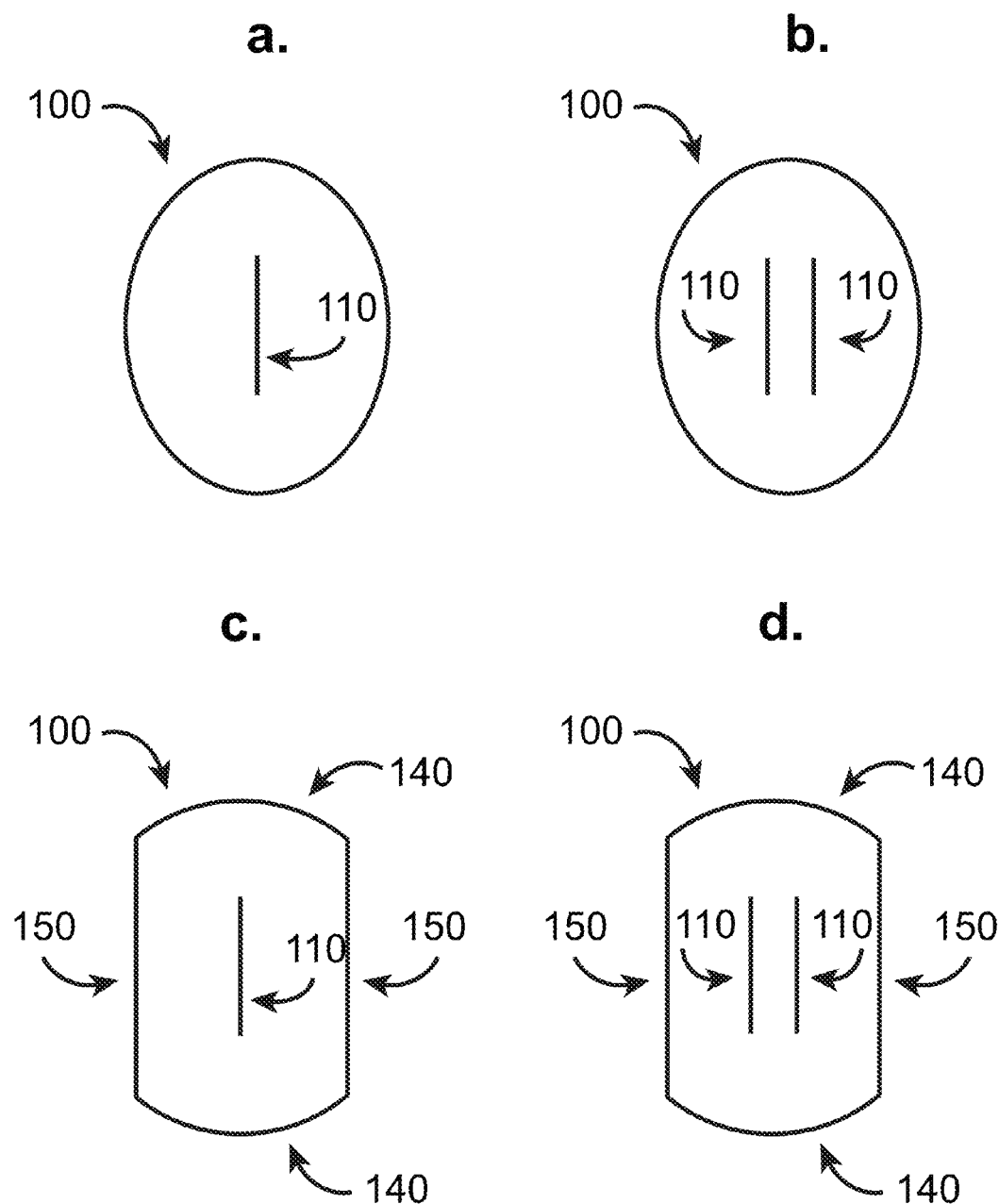
FIGS. 4a-d show top views of flexible membranes with elongated shapes according to certain embodiments of the present invention.

In alternate embodiments, such as those shown in FIG. 4, the membrane does not include tabs, but instead has an oval or oblong shape such that the widest part of the membrane is in-line with the longitudinal axis of a linear slit or slits. For example, in FIGS. 4a-b, the flexible membrane 100 has an elliptical shape, with the long axis of the ellipse corresponding to the axis of the linear slit or slits 110. In this arrangement, membrane-securement features selectively compress, stretch or fold the edges of the flexible membrane 100 that are in-line with the linear slit(s) 110. Alternatively, as shown in FIG. 4c-d, the flexible membrane 100 incorporates curved edges 140 in-line with the axis defined by linear slit(s) 110, and straight edges 150, which are parallel to the axis defined by linear slit 110. In this arrangement, membrane securement features selectively compress, stretch, or fold the curved edges 140 of the flexible membrane 100 in order to achieve the desired tension.

Figure 2:
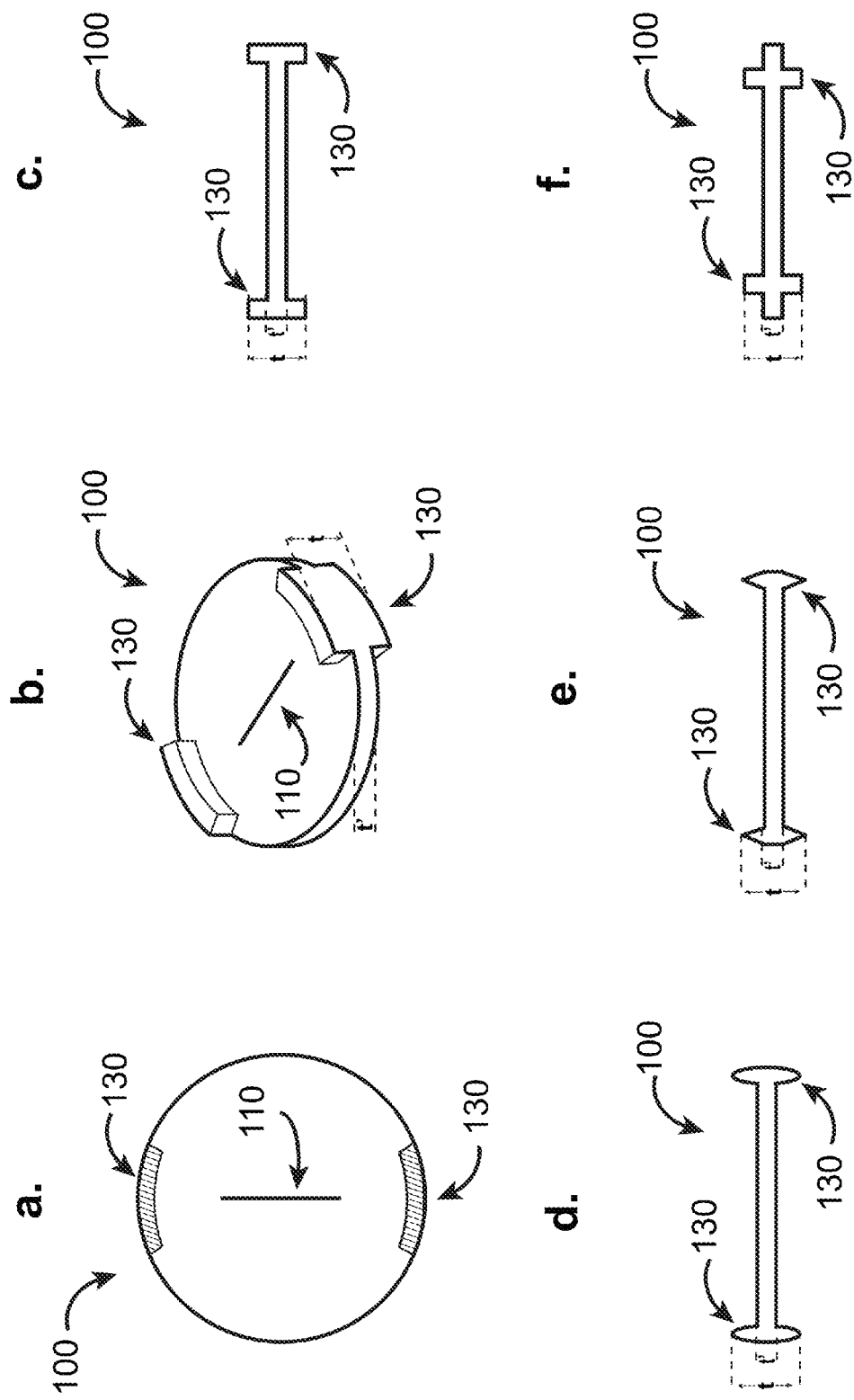
FIGS. 2a-f show schematic depictions of flexible membranes of varying thickness in accordance with certain embodiments of the present invention.

In certain embodiments, tension along the axis of the linear slit is achieved, in part, by increasing the thickness of a portion or portions of the flexible membrane about an axis defined by a slit in the flexible membrane is increased relative to the rest of the membrane. For example, in the embodiment shown in FIGS. 2a-c, flexible membrane 100 incorporates two edge regions 130 positioned in-line with the linear slit 110, which edge regions have a first thickness, t. The remainder of the flexible membrane, including the linear slit 110, is characterized by a second thickness, t', which is less than the first thickness t. The cross-sectional geometry of the edge region 130 may be square as in FIG. 2c, rounded as in FIG. 2d, angular as in FIG. 2e, or any other geometry suitable for the application of tension to the flexible membrane 100 longitudinally along an axis defined by a linear slit 110. In addition, as shown in FIG. 2f, it is not necessary that the portion of the flexible membrane having the greatest thickness be positioned at the edge of the flexible membrane 100, as long as the thickest area of the membrane is in-line with a linear slit. When force is applied to the edge regions 130—for example by membrane securement features—along a vector that is directed radially outward from the center of flexible membrane 100, tension is applied along the axis defined by the linear slit or slits 110.

Figure 5:
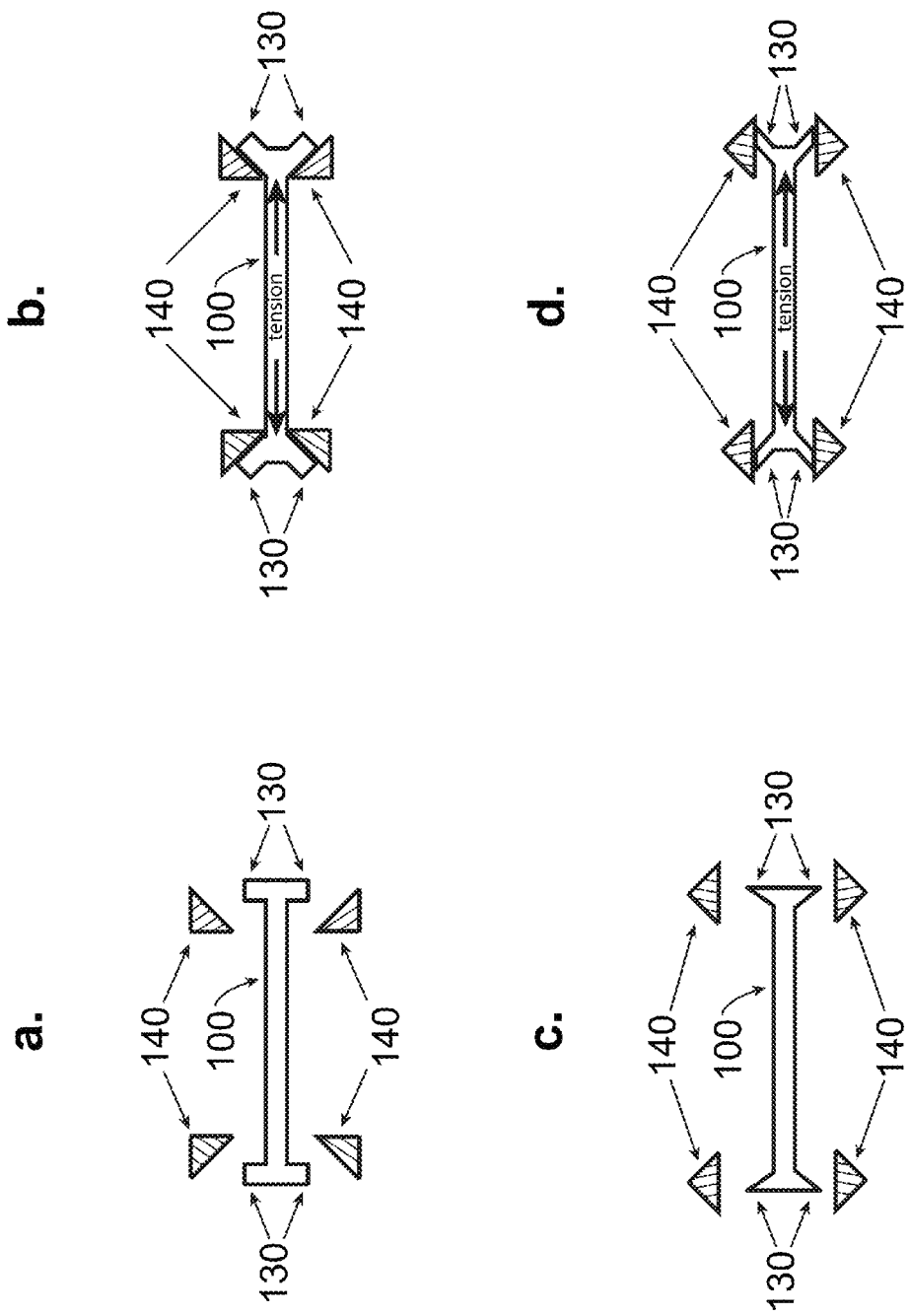
FIGS. 5a-d show side view schematic depictions of tension being applied to flexible membranes according to certain embodiments of the present invention.

Compressive force is applied to the edge regions 130 in different ways. In certain embodiments, as illustrated in FIG. 5 a-b, the membrane-securement features 140 have at least one compression surface that is angled relative to the surface of the flexible membrane 100 such that, when the membrane securement features 140 are in contact with the edge regions 130, said edge regions 130 are simultaneously compressed both inwardly (i.e. in a direction perpendicular to and incident on the surfaces of membrane 100), and radially outward, creating tension along the longitudinal axis of membrane 100 defined by the linear slit or slits 110. In alternate embodiments such as those shown in FIG. 5c-d, the edge regions 130 have a cross-sectional geometry which is biased toward the outer edge of flexible membrane 100. When compressive force is applied along a vector that is perpendicular to the surfaces of the membrane, the edge regions 130 will tend to be displaced radially outward, applying tension to membrane 100 along the longitudinal axis defined by the linear slit or slits 100.

In certain embodiments, tension is selectively applied to the flexible membrane about the axis defined by a linear slit by compressing or folding the edge of the membrane and providing an adjacent space into which the edge of the membrane can be displaced. By varying the degree of displacement, the tension on the membrane may be varied. In a preferred embodiment, as shown in FIG. 3, a valve 300 includes a flexible membrane 100 according to an embodiment of the present invention, for example as illustrated in FIG. 1, 4, or 3c, and valve housing 200 having first and second valve housing portions 210, 220, which have first and second mating surfaces 211, 221. In the preferred embodiment depicted in FIGS. 3d-g, the first and second valve housing portions have primary pinch surfaces 212, 222 which are substantially parallel to the surfaces of the flexible membrane 100 and which apply compressive pressure to the flexible membrane 100 when the valve 200 is fully assembled. The first valve housing portion 210 has a secondary pinch surface 213 which is at an angle $\Phi$ relative to the first pinch surface 212. An open space 230 is defined by one or both of the first and second valve housing portions 210, 220, which is proximate to the second pinch surface 212. As shown in FIGS. 3d and e, when the assembled valve 300 is viewed in cross-section along an axis AA which is parallel to the linear slit or slits 110 in flexible membrane 100, the flexible membrane extends through and is compressed by the primary pinch surfaces 212, 222, and the edge of the flexible membrane 100 is displaced by the secondary pinch surface 213 into the open space 230, such that tension is applied to the flexible membrane 100 in a radially outward direction. A benefit of this design is that, during assembly, the secondary pinch surface 213 engages the flexible membrane 100 before the primary pinch surfaces 212, 222, directing tension in line with the slit by forcing the edge of the flexible membrane 100 into the open space 230. By contrast, when the valve 300 is viewed in cross section along an axis BB (as shown in FIGS. 3f and g), which is perpendicular to the linear slit or slits 110 in flexible membrane 100, the flexible membrane 100 only extends far enough to engage with the primary pinch surfaces 212, 222, while the angled secondary pinch surface 213 blocks the edge of the membrane so no radial outward tension is applied and so that the edge of the flexible membrane 100 is inhibited from outward movement.

In certain embodiments such as those shown in FIG. 3, altering the angle of the secondary pinch surface 213 relative to the primary pinch surface 212 has different results at different portions of the edge of the flexible membrane 100. When viewed in cross-section along axis AA, as shown in FIGS. 3 d and e, changing the angle of the face of the secondary pinch point 213 alters the amount of radial tension and compressive force applied to the flexible membrane 100: a smaller angle results in greater radial tension and securing force; a larger angle results in less radial tension and securing force. When viewed in cross-section along axis BB, as shown in FIGS. 3 f and g, decreasing the angle results in less room for outward displacement of the edge of flexible membrane 100.

In embodiments as shown in FIG. 3, the space between the primary pinch surfaces 212, 222 may be constant or may vary along the inner surface of valve 300. Maintenance of a constant space between the primary pinch surfaces 212, 222 can be achieved by incorporating a hard stop between the first and second valve housing portions 210, 220. In certain embodiments, the mating surfaces 211, 221 at the hard stop are configured to be laser welded together rather than glued. A press-fit can also be incorporated between the first and second valve housing portions 210, 220 as either a primary attachment means, or as a secondary means in conjunction with gluing or laser welding. Utilization of a press-fit can be used for in-process assembly of valves prior to final welding or adhesion, for preliminary performance testing or other purposes.

These embodiments have been described in an exemplary manner, and are not intended to limit the scope of the invention which is intended to cover all modifications and variations of this invention that come within the scope of the appended claims and their equivalents. The specification is, therefore, to be regarded in an illustrative rather than a restrictive sense.

We claim:

1. A pressure activated valve, comprising:
   a flexible membrane having at least one linear slit therethrough, the membrane being under tension along a longitudinal axis defined by the at least one linear slit;
   wherein the longitudinal axis comprises two or more portions with a thickness greater than the remaining flexible membrane.

2. A pressure activated valve, comprising:
   a flexible membrane having at least one linear slit therethrough, the membrane being under tension along a longitudinal axis defined by the at least one linear slit;
   wherein the flexible membrane comprises one or more tabs that extend along the longitudinal axis, such that a length of the longitudinal axis is greater than a length of a bisecting latitudinal axis; and
   wherein a valve housing and the flexible membrane are configured to apply a tensioning force along the first axis and extending away from the second axis.

3. A pressure activated valve, comprising:
   a valve housing defining a lumen, the valve housing comprising:
      a first valve housing portion having a first mating surface; and
      a second valve housing portion having a second mating surface in contact with the first mating surface; and
   a flexible membrane disposed within the lumen, the flexible membrane having a first slit therethrough;
   wherein the first slit lies along a first axis of the flexible membrane, the first axis perpendicularly bisecting a second axis;
   wherein the flexible membrane comprises one or more tabs that extend along the first axis, such that a length of the first axis is greater than a length of the second axis; and
   wherein the valve housing and the flexible membrane are configured to apply a tensioning force along the first axis and extending away from the second axis.

4. The pressure activated valve of claim 3, wherein the flexible membrane is oval.

5. The pressure activated valve of claim 3, wherein the membrane is circular.

6. The pressure activated valve of claim 3, wherein the valve housing further comprises membrane securing features.

7. The pressure activated valve of claim 3, wherein the first and second mating surfaces are configured to displace a portion of the edge of the flexible membrane at a nonzero angle relative to a plane that is substantially parallel to a surface of the flexible membrane.

8. The pressure activated valve of claim 3, wherein at least one of the first and second mating surfaces defines a space sized to accommodate a portion of an edge of the flexible membrane therein, and wherein the space is situated along the first axis.

9. The pressure activated valve of claim 8, wherein the one or more tabs are rectangular.

10. A pressure activated valve comprising:
    a valve housing defining a lumen, the valve housing comprising:
       a first valve housing portion having a first mating surface; and
       a second valve housing portion having a second mating surface in contact with the first mating surface; and
    a flexible membrane disposed within the lumen, the flexible membrane having a first slit therethrough;
    wherein the first slit lies along a first axis of the flexible membrane, said first axis having two or more portions with a thickness greater than a thickness along a second axis of the flexible membrane, the second axis perpendicularly bisecting the first axis; and
    wherein the valve housing and the flexible membrane are configured to apply a tensioning force along the first axis and extending away from the second axis.

11. The pressure activated valve of claim 10, wherein at least one of the first and second mating surfaces defines a space sized to accommodate a portion of an edge of the flexible membrane.

12. The pressure activated valve of claim 10, wherein the two or more portions are edges of the flexible membrane.

13. The pressure activated valve of claim 12, wherein the two or more edges have rounded cross-sectional geometry.

14. The pressure activated valve of claim 12, wherein the two or more edges have square cross-sectional geometry.

15. The pressure activated valve of claim 14, wherein the valve housing further comprises membrane securing features.

* * * * *